United States Patent [19]
Morgan, Jr.

[11] Patent Number: 4,498,464
[45] Date of Patent: Feb. 12, 1985

[54] CHIROPRACTIC INSTRUMENT

[76] Inventor: Darrell W. Morgan, Jr., 53-780 Avenida Diaz, La Quinta, Calif. 92253

[21] Appl. No.: 390,235

[22] Filed: Jun. 21, 1982

[51] Int. Cl.³ .......... A61N 23/00

[52] U.S. Cl. .......... 128/54; 145/29 B; 145/36; 128/61

[58] Field of Search .......... 128/54, 32, 34, 42, 128/43, 60, 61, 67, 740; 241/5; 81/463; 145/29 A 29 B, 36; 30/277; 273/170; 101/406; 446/398, 402, 400; 42/1 H

[56] References Cited

U.S. PATENT DOCUMENTS

| | | | |
|---|---|---|---|
| 1,385,490 | 7/1921 | Perez | 101/405 |
| 2,664,820 | 1/1954 | Brown, Jr. | 101/405 |
| 2,970,592 | 2/1961 | David | 128/54 |
| 3,589,731 | 6/1971 | Chancellor, Jr. | 273/170 |
| 3,710,655 | 1/1973 | Brandle | 81/463 |
| 3,783,956 | 1/1974 | Schultz | 81/463 |
| 4,039,012 | 8/1977 | Cook | 273/170 |

FOREIGN PATENT DOCUMENTS

| | | | |
|---|---|---|---|
| 736275 | 11/1932 | France | 128/54 |
| 924131 | 7/1947 | France | 81/463 |

*Primary Examiner*—Richard J. Apley
*Assistant Examiner*—Harry Macey
*Attorney, Agent, or Firm*—Edgar W. Averill, Jr.

[57] ABSTRACT

A chiropractic instrument for adjusting a patient's spine by striking the instrument against the vertebrae of the spine. The instrument has an elongated body piece with a longitudinal opening. The longitudinal opening contains a spring and two elongated members. When the instrument is struck against a patient, one of the elongated members moves to compress the spring and imparts a force through the instrument.

7 Claims, 3 Drawing Figures

CHIROPRACTIC INSTRUMENT

BACKGROUND OF THE INVENTION

The field of the invention is chiropractic instruments and the invention relates more particularly to instruments of the type which are used to adjust a patient's spine. Numerous instruments have been used for the purpose of providing a controlled striking force against a portion of a patient's body. Instruments used for testing reflex action in order to determine the reaction sensitivity of a patient's nervous system are disclosed in U.S. Pat. Nos.: 2,800,895, 3,185,146, and 3,626,927. Other tools for providing a striking force with increased impact are utilized in metal working and such devices are shown in U.S. Pat. Nos. 3,130,762, 3,172,438 and 4,039,012.

There is a need, however, for an instrument which provides improved control by a chiropractor or other practitioner to provide the desired amount of impact to a patient. Whereas devices such as that shown in the Torricelli Hand Reflex Gun, U.S. Pat. No. 2,800,895, utilize a spring with markings which permit the user to compress the spring in a predetermined amount, it is believed that this does not provide sufficient feel for the doctor to provide an appropriate amount of impact.

There is thus a need for an instrument which provides the practitioner with an improved amount of sensitivity to enable him to provide a predetermined proper amount of impact against a patient.

SUMMARY OF THE INVENTION

It is an object of the present invention to provide a chiropractic instrument which enables the user to impart an accurate amount of impact to a patient.

The present invention is for a chiropractic instrument for adjusting a patient's spine by striking the instrument against the vertebrae of the spine. The instrument has an elongated body piece having a striking end and a second end. A longitudinal opening is formed axially in the elongated body piece, said opening terminating near the striking end at one end of the instrument and near the second end at the other end of the opening. Spring means are positioned in the opening and said spring means rest at the end of the opening near the striking end. The spring means are positioned with its outer surface near the inner surface of the longitudinal opening. A first elongated member is positioned within the spring means and the first elongated member is shorter than the spring means so that the spring extends upwardly past the end of the first elongated member when both the spring means and the first elongated member are resting against the terminating end of the longitudinal opening. A second elongated means, larger in outside diameter than the inside diameter of the spring means, rests at one end against the upper end of the spring means and at the other end against the terminating end of the longitudinal opening. A striking foot is located at the striking end of the device whereby when the device is struck against an object, the force of inertia moves the second elongated means toward the striking foot compressing the spring and finally resulting in the second elongated means striking the first elongated member and imparting an impact force to the striking foot.

DESCRIPTION OF THE PREFERRED EMBODIMENTS

Figure 1:
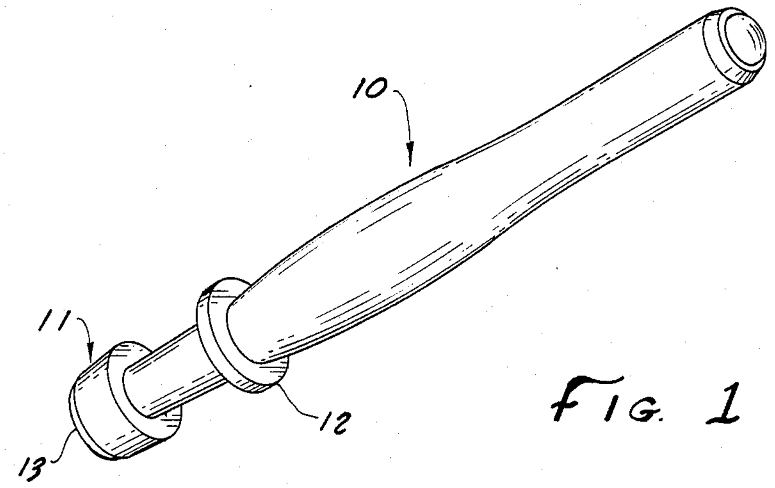
FIG. 1 is a perspective view of the instrument of the present invention.
Figure 2:
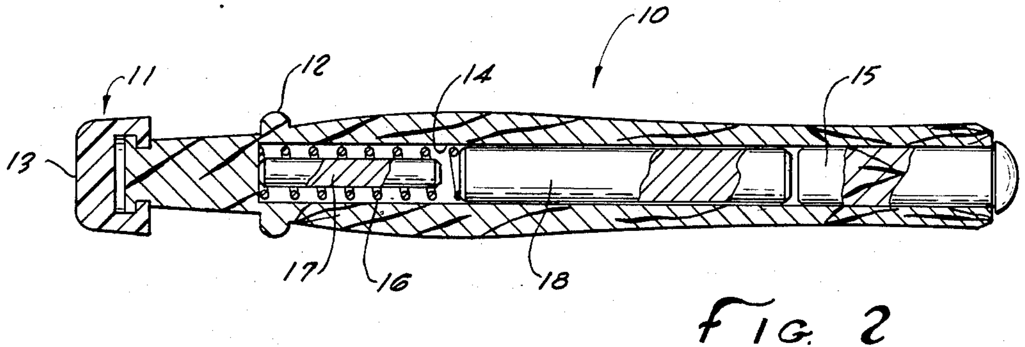
FIG. 2 is a cross-sectional side view of the instrument of FIG. 1.

The chiropractic instrument of the present invention is shown in FIG. 1 and indicated generally by reference character 10. The instrument has a rubber striking foot 11 at its striking end and a control ring 12 positioned near the striking end 13 of instrument 10.

Instrument 10 is preferably fabricated from wood which is both light in weight and provides a non-slippery surface for use by the practitioner. Other materials of construction such as plastic or even metal could, however, be used in place of wood.

The instrument 10 has a longitudinal opening 14 which is positioned along the longitudinal axis of the instrument. A wooden plug 15 is glued or otherwise affixed at the open end of longitudinal opening 14 to permanently close this end.

There are three elements within the longitudinal opening. The first is a helical compression spring 16 which surrounds a first longitudinal member 17 which may be a metal pin. Spring 16 extends beyond the end of longitudinal member 17 for reasons described below. A second longitudinal member 18 is positioned in opening 14 and is sufficiently small in outside diameter so that it may move freely along the longitudinal opening except as impaired by spring 16 and first longitudinal member 17.

Figure 3:
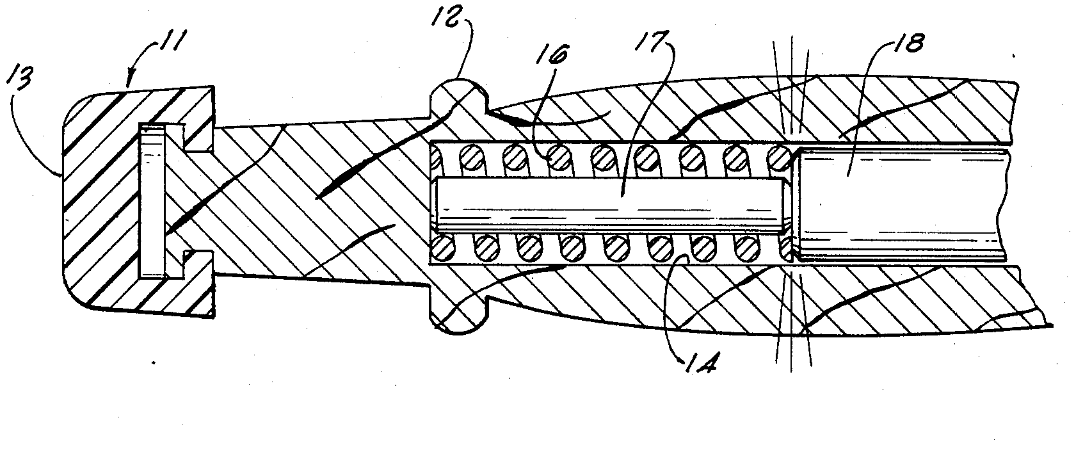
FIG. 3 is an enlarged cross-sectional view of the striking end of the instrument of FIG. 1.

In use, the instrument is held in the practitioner's hand preferably between the thumb and forefinger, and the striking end 13 is struck against the patient's vertebrae. Upon striking any object such as a vertebrae, the second longitudinal member 18 moves toward striking end 13 compressing spring 16 until it strikes first longitudinal member 17 as shown in FIG. 3. This imparts an impact through the striking foot 11 to the patient's vertebrae to provide the desired movement of the vetebrae. The ability of the practitioner to control the striking force by the movement of his wrist and hand permits a very accurate amount of impact to be imparted and provides a safe yet effective method for chiropractic manipulation of the spine.

While the striking foot is shown as a separate rubber or other elastomeric material, it is possible that for some applications this striking foot may merely form the wood end of the instrument although the elastomeric foot is preferred to cushion the blow. While the control ring is a preferred improvement, the instrument may be utilized, of course, without such control ring. The mass of the second longitudinal member is an important element of the present invention and it has been found that for an instrument having an overall length of 6 inches and an opening with an inside diameter of slightly greater tan 5/16 of an inch that a steel pin having an outside diameter of 5/16 of an inch and a length of $2\frac{1}{4}$ inches has proved satisfactory. Spring 16 should hold the second longitudinal member against the wooden plug 15 when the instrument is lying on its side and yet should be sufficiently flexible so that the second longitudinal member 18 will compress the spring permitting the member 18 to strike the first longitudinal member 17. A final elongated member comprising a steel pin having an outside diameter of about 3/16 of an inch and a length of about $1\frac{1}{8}$ inch is preferred. A spring length of $1\frac{5}{8}$ inches and an opening length of $3\frac{1}{2}$ inches has proved very satisfactory. While the instrument of the present invention is particularly well adapted for spine adjustment, it is also very useful to adjust other articulations.

The present embodiments of the invention are thus to be considered in all respects as illustrative and not restrictive, the scope of the invention being indicated by the appended claims rather than by the foregoing description. All changes which come within the meaning and range of equivalency of the claims therefore are intended to be embraced therein.

What is claimed is:

1. A chiropractic instrument for adjusting a patient's spine by striking the instrument against the vertebrae of the spine, said instrument comprising:

an elongated body piece having a striking end and a second end;

a longitudinal bore formed axially in said elongated body piece, said bore having a first termination end wall near said striking end at one end of the bore and having a second termination end wall near the second end at the other end;

helical spring means having a first end and a second end, said helical spring means being positioned in said bore, said helical spring means having its first end resting against the first termination end wall and said spring means being positioned with its outer surface near the inner surface of the bore and having a longitudinal opening along its center;

a first elongated member positioned within said spring means, said first elongated member being longitudinally shorter than the free length of the helical spring means so that the helical spring means extends beyond the end of the first elongated member when both the spring means and the first elongated member are resting against the first termination end wall;

a second elongated means, unattached to any portion of the instrument and being larger in outside diameter than the longitudinal opening in said helical spring means, and resting at one end against the the second end of the helical spring means and spaced away from said first elongated member when the instrument is at rest, said second elongated means being longitudinally moveable within said longitudinal bore and being held completely within said bore; and a blunt striking foot located at the striking end of the device whereby when the device is struck against a patient's spine, the second elongated means compresses the helical spring means by inertia and strikes the end of the first elongated means transmitting energy to the striking foot.

2. The chiropractic instrument of claim 1 further including a circular protrusion located near the striking end of said instrument to provide improved grip of the user along the instrument.

3. The chiropractic instrument of claim 1 wherein said first elongated member is permitted to move freely within said spring means.

4. The chiropractic instrument of claim 1 wherein said striking foot is an elastomeric striking foot.

5. The chiropractic instrument of claim 1 wherein the body of said instrument is formed from wood.

6. The chiropractic instrument of claim 1 wherein said second elongated means comprises a steel rod having an outside diameter of about 5/16 of an inch and a length of about $2\frac{1}{4}$ inches.

7. The chiropractic instrument of claim 1 wherein said first elongated member comprises a steel pin having an outside diameter of about 3/16 of an inch and a length of about $1\frac{1}{8}$ inches.

* * * * *